United States Patent [19]

Holmwood et al.

[11] Patent Number: 4,645,767
[45] Date of Patent: * Feb. 24, 1987

[54] HYDROXYETHYL-AZOLE DERIVATIVES AND FUNGICIDAL USE THEREOF

[75] Inventors: Graham Holmwood; Wolfgang Krämer, both of Wuppertal; Karl H. Büchel, Burscheid; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[*] Notice: The portion of the term of this patent subsequent to Nov. 11, 2003 has been disclaimed.

[21] Appl. No.: 650,965

[22] Filed: Sep. 14, 1984

[30] Foreign Application Priority Data

Sep. 26, 1983 [DE] Fed. Rep. of Germany ....... 3334779

[51] Int. Cl.$^4$ ................... A01N 43/50; A01N 43/653; C07D 233/60; C07D 249/08
[52] U.S. Cl. .................................. 514/383; 514/184; 514/399; 548/101; 548/262; 548/341
[58] Field of Search ....................... 548/262, 341, 101; 514/184, 383, 399

[56] References Cited

U.S. PATENT DOCUMENTS 4,507,140 3/1985 Sugavanam .......................... 514/383

FOREIGN PATENT DOCUMENTS 0040345 11/1981 European Pat. Off. ............ 548/262
3202602 8/1983 Fed. Rep. of Germany ...... 548/262
2114120 8/1983 United Kingdom ................ 548/262

Primary Examiner—Richard L. Raymond
Attorney, Agent, or Firm—Sprung, Horn, Kramer & Woods

[57] ABSTRACT

Hydroxyethyl-azole derivatives of the formula

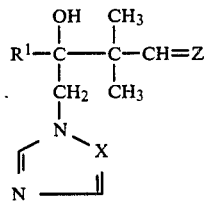

in which
R$^1$ represents alkyl or the grouping Ar—Y—,
Ar represents optionally substituted aryl,
X represents a nitrogen atom or the CH group,
Y represents a direct bond or the grouping —CH$_2$—, —CH$_2$CH$_2$—, —OCH$_2$—, —SCH$_2$—, —CH=CH— or —C≡C—,
Z represents oxygen or the NOR$^2$ group and
R$^2$ represents hydrogen, alkyl, alkenyl, alkinyl, optionally substituted aralkyl or optionally substituted cycloalkylalkyl, or addition products thereof with acids or metal salts, which possess fungicidal activity.

9 Claims, No Drawings

HYDROXYETHYL-AZOLE DERIVATIVES AND FUNGICIDAL USE THEREOF

The present invention relates to new hydroxyethyl-azole derivatives, several processes for their preparation and their use as fungicides.

It has already been disclosed that certain hydroxyethyl-azole derivatives, such as, for example, 1-(2,4-dichlorophenoxy)-3,3-dimethyl-2-(1,2,4-triazol-1-yl-methyl)-2-butanol or 1-(4-chlorophenoxy)-3,3-dimethyl-2-(imidazol-1-yl)-2-butanol, have fungicidal properties (compare European No. 0,040,345 corresponding to U.S. Application Ser. No. 499,679 filed June 6, 1983, now pending.) However, the effectiveness of these compounds is not always completely satisfactory, especially when low amounts and concentration are applied.

New hydroxyethyl-azole derivatives of the general formula (I)

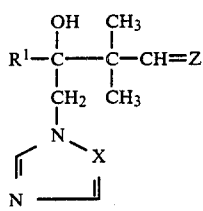

(I)

in which
  $R^1$ represents alkyl or the grouping Ar—Y—,
  Ar represents optionally substituted aryl,
  X represents a nitrogen atom or the CH group,
  Y represents a direct bond or the grouping —$CH_2$—, —$CH_2CH_2$—, —$OCH_2$—, —$SCH_2$—, —CH=CH— or —C≡C—,
  Z represents oxygen or the $NOR^2$ group and
  $R^2$ represents hydrogen, alkyl, alkenyl, alkinyl, optionally substituted aralkyl or optionally substituted cycloalkylalkyl,
and acid addition salts and metal salt complexes thereof, have now been found.

It has furthermore been found that the hydroxyethyl-azole derivatives of the formula (I) are obtained when
  (a) hydroxyethylazolyl-acetal derivatives of the formula (II)

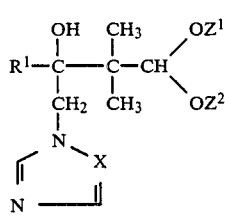

(II)

in which
  $Z^1$ and $Z^2$ represent alkyl or, together with the oxygen atom to which they are bonded, represent a dioxolane ring; and
  $R^1$ and X have the abovementioned meaning,
are heated in the presence of a mixture of water and an organic solvent and in the presence of an acid; and/or
  (b) the hydroxyethyl-azole derivatives, obtained by process (a), of the formula (Ia)

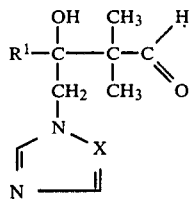

(Ia)

in which
  $R^1$ and X have the abovementioned meaning, or the hydroxyethylazolyl-acetal derivatives of the formula (II) are reacted with hydroxylamine derivatives of the formula (III)

$$H_2N—O—R^2 \quad (III)$$

in which
  $R^2$ has the abovementioned meaning, in the presence of a diluent; or
  (c) the hydroxyethyl-azole derivatives, obtained by process (b), of the formula (Ib) (that is to say those compounds of the formula (I) in which Z represents the NOH group)

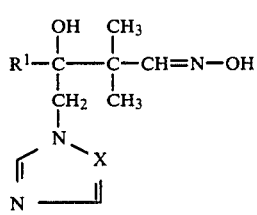

(Ib)

in which
  $R^1$ and X have the abovementioned meaning, are reacted with halides of the formula (IV)

$$Hal—R^3 \quad (IV)$$

in which
  Hal represents chlorine, bromine or iodine and
  $R^3$ represents the meanings of $R^2$, with the exception of hydrogen,
in the presence of a diluent and if appropriate in the presence of a base; or
  (d) oxiranes of the formula (V)

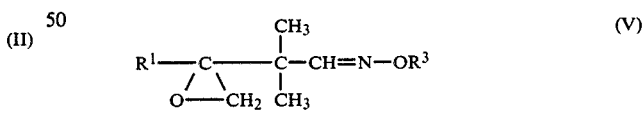

(V)

in which
  $R^1$ and $R^3$ have the abovementioned meanings, are reacted with azoles of the formula (VI)

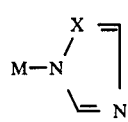

(VI)

in which
  M represents hydrogen or an alkali metal, in the presence of a diluent and if appropriate in the presence of a base.

If appropriate, an acid or a metal salt can then be added on the compounds of the formula (I) thus obtained.

The new hydroxyethyl-azole derivatives of the formula (I) have powerful fungicidal properties. Surprisingly, the compounds according to the invention exhibit a more powerful action than the hydroxyethyl-azole derivatives 1-(2,4-dichlorophenoxy)-3,3-dimethyl-2-(1,2,4-triazol-1-yl-methyl)-2-butanol and 1-(4-chlorophenoxy)-3,3-dimethyl-2-(imidazol-1-yl)-2-butanol, which are known from the prior art and are closely related compounds structurally and from the point of view of their action. The substances according to the invention thus represent an enrichment of the art.

Formula (I) provides a general definition of the hydroxyethyl-azole derivatives according to the invention.

Preferably, in this formula, $R^1$ represents straight-chain or branched alkyl with 1 to 6 carbon atoms or the grouping Ar—Y; Ar represents naphthyl, or represents phenyl which is optionally monosubstituted or polysubstituted by identical or different substituents, preferred substituents which may be mentioned being: halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, such as, preferably, fluorine and chlorine atoms, the —CH=NOR$^2$ radical, and phenyl, phenoxy, benzyl and benzyloxy, in each case optionally substituted by halogen and or alkyl with 1 or 2 carbon atoms;

X represents a nitrogen atom or the CH group;

Y represents a direct bond or the grouping —CH$_2$—, —CH$_2$CH$_2$—, —OCH$_2$—, —SCH$_2$—, —CH=CH— or —C≡C—;

Z represents oxygen or the NOR$^2$ group; and $R^2$ represents hydrogen, straight-chain or branched alkyl with 1 to 6 carbon atoms or alkenyl or alkinyl with in each case 2 to 6 carbon atoms, or represents phenylalkyl which has 1 or 2 carbon atoms in the alkyl part and is optionally monosubstituted or polysubstituted by identical or different substituents, possible substituents on the phenyl being the substituents on the phenyl already mentioned for Ar; or represents cycloalkylmethyl which has 5 or 6 carbon atoms in the cycloalkyl part and is optionally mono-, di- or tri-substituted by identical or different alkyl radicals with 1 to 3 carbon atoms.

Particularly preferred compounds of the formula (I) are those
in which $R^1$ represents straight-chain alkyl with 1 to 6 carbon atoms or the grouping Ar—Y—;

Ar represents naphthyl, or represents phenyl which is optionally mono- di- or tri-substituted by identical or different substituents, substituents which may be mentioned being: fluorine, chlorine, methyl, trifluoromethyl, trifluoromethoxy, trifluoromethylthio, methoximinomethyl, ethoximinomethyl and allyloximinomethyl, and phenyl, phenoxy, benzyl and benzyloxy, in each case optionally substituted by chlorine and/or methyl;

X represents a nitrogen atom or the CH group;

Y represents a direct bond or the grouping —CH$_2$—, —CH$_2$CH$_2$—, —OCH$_2$—, —SCH$_2$—, —CH=CH— or —C≡C—; and Z represents oxygen or the NOR$^2$ group,
wherein $R^2$ represents hydrogen, methyl, ethyl, n-propyl, n-butyl, allyl or propargyl, or represents benzyl which is optionally mono-, di- or tri-substituted by identical or different substituents from the group comprising fluorine, chlorine, methyl, trifluoromethyl and trifluoromethoxy, or represents cyclohexylmethyl which is optionally substituted by methyl or ethyl.

Addition products of acids and those hydroxyethyl-azole derivatives of the formula (I) in which the substitutents $R^1$, X and Z have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main groups II to IV and of sub-groups I and II and IV to VIII and those substituted hydroxyethyl-azole derivatives of the formula (I) in which the substituents $R^1$, X and Z have the meanings which have already been mentioned as preferred to these substituents are also preferred compounds according to the invention.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and furthermore phosphoric acid, nitric acid and sulphuric acid.

The following compounds of the general formula (I) may be mentioned specifically, in addition to the compounds mentioned in the preparation examples:

$$R^1-\underset{\underset{\underset{N}{\overset{|}{N}}}{\overset{|}{\underset{CH_2}{|}}}}{\overset{OH}{\overset{|}{C}}}-\underset{CH_3}{\overset{CH_3}{\overset{|}{C}}}-CH=Z \qquad (I)$$

(wherein X represents either a nitrogen atom or the CH group):

| $R^1$ | Z |
|---|---|
| 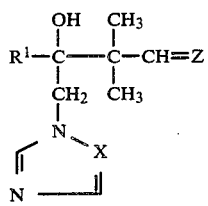 | O |

| R¹ | Z |
|---|---|
| 2,4-dichlorophenyl-O-CH₂- | N-OCH₃ |
| biphenyl-CH₂CH₂- | O |
| biphenyl-CH₂CH₂- | N-OCH₃ |
| biphenyl-CH=CH- | O |
| biphenyl-CH=CH- | N-OCH₃ |
| CH₃ | N-O-CH₂-(2,4-dichlorophenyl) |
| C₂H₅ | N-O-CH₂-(2,4-dichlorophenyl) |
| C₃H₇ | N-O-CH₂-(2,4-dichlorophenyl) |
| C₄H₉ | N-O-CH₂-(2,4-dichlorophenyl) |
| C₄H₉ | N-O-CH₂-(2,4-dichlorophenyl) |
| C₄H₉ | N-O-CH₂-cyclohexyl |
| 4-Cl-C₆H₄-CH₂-CH₂- | N-O-CH₃ |
| 4-Cl-C₆H₄-CH₂-CH₂- | N-O-C₂H₅ |
| 4-Cl-C₆H₄-CH₂-CH₂- | N-O-C₃H₇ |
| 4-Cl-C₆H₄-CH₂-CH₂- | N-O-C₄H₉ |
| 4-Cl-C₆H₄-CH₂-CH₂- | N-O-CH=CH₂ |
| 4-Cl-C₆H₄-CH₂-CH₂- | N-O-CH₂-(4-Cl-C₆H₄) |
| 4-Cl-C₆H₄-CH₂-CH₂- | N-O-CH₂-(2,4-dichlorophenyl) |
| 4-Cl-C₆H₄-S-CH₂- | N-O-CH₃ |
| 4-Cl-C₆H₄-S-CH₂- | N-O-CH₂-CH=CH₂ |
| 2,4-dichlorophenyl-O-CH₂- | N-OCH₃ |
| 2,4-dichlorophenyl-O-CH₂- | N-O-CH₂-(4-Cl-C₆H₄) |
| 2,4-dichlorophenyl-O-CH₂- | N-O-C₄H₉ |
| 2,4-dichlorophenyl- | N-OCH₃ |
| 2,4-dichlorophenyl- | N-OC₂H₅ |
| 2,4-dichlorophenyl- | N-OC₃H₇ |
| 2,4-dichlorophenyl- | N-OC₄H₉ |
| 2,4-dichlorophenyl- | N-O-CH₂-CH=CH₂ |
| biphenyl- | N-OCH₃ |
| 2-F-4-Cl-phenyl- | N-OCH₃ |

If, for example, 1-(4-chlorophenoxy)-3-(1,3-dioxolan-2-yl)-3-methyl-2-(1,2,4-triazol-1-yl-methyl)-2-butanol in an ethanol/water mixture is used as the starting substance, the course of process (a) according to the invention can be represented by the following equation:

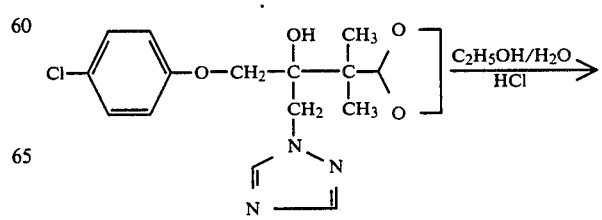

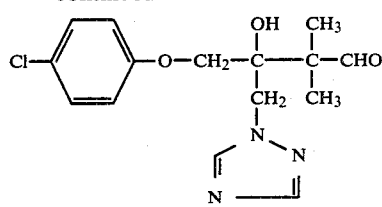

If, for example, 4-(4-chlorophenoxy)-2,2-dimethyl-3-hydroxy-3-(1,2,4-triazol-1-yl-methyl)-butanal and O-methyl-hydroxylamine hydrochloride are used as starting substances, the course of process (b) according to the invention can be represented by the following equation:

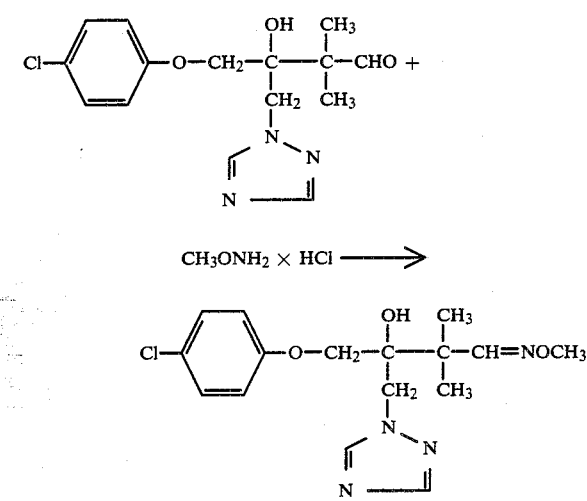

If, for example, 1-(4-chlorophenoxy)-3-hydroximino-methyl-3-methyl-2-(1,2,4-triazol-1-yl-methyl)-2-butanol and 4-chlorobenzyl chloride are used as starting substances, the course of process (c) according to the invention can be represented by the following equation:

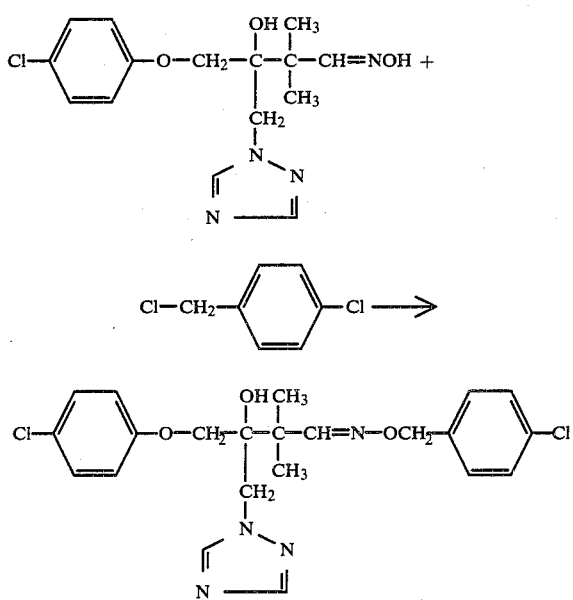

If, for example, 2-(2,4-dichlorophenyl)-2-(2-methoximinomethyl-2-propyl)-oxirane and 1,2,4-triazole are used as starting substances, the course of process (d) according to the invention can be represented by the following equation:

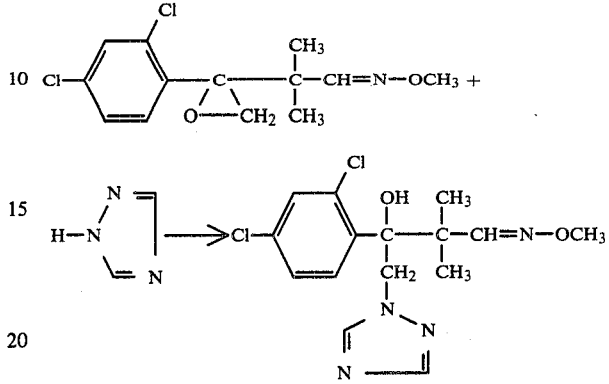

Formula (II) provides a general definition of the hydroxyethylazolyl-acetal derivatives to be used as starting substances for carrying out process (a) according to the invention. In this formula, $R^1$ and X preferably have the meanings which have already been mentioned as preferred for these substituents in connection with the description of the substances of the formula (I) according to the invention. $Z^1$ and $Z^2$ preferably represent alkyl with 1 to 4 carbon atoms, such as, in particular, methyl, or, together with the oxygen atoms in which they are bonded, represent a dioxolane ring.

The hydroxyethylazolyl-acetal derivatives of the formula (II) are the subject of German Patent Application No. P 32 42 222 filed Nov. 15, 1982 and Application Ser. No. 547,807 filed Nov. 1, 1983, now pending, corresponding to German Application No. P 32 42 252 filed Nov. 15, 1982; or they can be obtained by the processes described therein, by reacting oxiranes of the formula (VII)

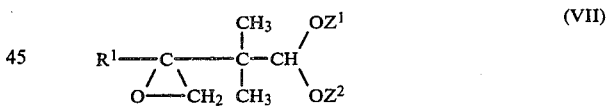

in which $R^1$, $Z^1$ and $Z^2$ have the abovementioned meaning, with azoles of the formula (VI) in the presence of an inert organic solvent, such as, for example, alcohols, and if appropriate in the presence of a base, such as, for example, a sodium alcoholate or potassium hydroxide, at temperatures between 60° C. and 150° C.

The oxiranes of the formula (VII) are the subject of Application Serial No. 547,807, supra; or they can be obtained in a generally known manner, by reacting ketones of the formula (VIII)

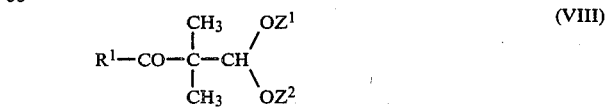

in which $R^1$, $Z^1$ and $Z^2$ have the abovementioned meaning, either (α) with dimethyloxosulphonium methylide of the formula (IX)

$$(CH_3)_2\overset{\delta+}{S}O\overset{\delta-}{C}H_2 \quad (IX)$$

in a manner which is known per se, in the presence of a diluent, such as, for example, dimethylsulphoxide, at temperatures between 20° C. and 80° C. (in this context, compare the statements in J. Am. Chem. Soc. 87, 1363-1364 (1965)), or (β) with trimethylsulphonium methyl-sulphate of the formula (X)

$$[(CH_3)_3S^{(+)}]\,CH_3SO_4^{(-)} \quad (X)$$

in a manner which is known per se, in the presence of an inert organic solvent, such as, for example, acetonitrile, and in the presence of a base, such as, for example, sodium methylate, at temperatures between 0° C. and 60° C., preferably at room temperature (compare also the statements in Heterocycles 8, 397 (1777)).

If appropriate, the oxiranes of the formula (VII) thus obtained can be further recited directly, without being isolated.

Some of the ketones of the formula (VIII) are known (compare, for example, J. Org. Chem. 32, 404 (1967)); of they are the subject of Application Ser. No. 503,102 filed June 10, 1983, now pending, corresponding to German Patent Application No. 32 24 130 filed June 29, 1982, Application Ser. No. 503,220 filed June 10, 1983, now pending, corresponding to German Patent Application No. P 32 24 129 filed June 30, 1982, and Application Ser. No. 547,806, supra; or they can be obtained in a known manner, for example by reacting 1-(N-morpholino-isobutene of the formula (XI)

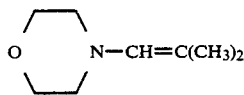

with chlorides of the formula (XII)

$$R^1-CO-Cl \quad (XII)$$

in which $R^1$ has the abovementioned meaning, in the presence of a solvent, such as, for example, diethyl ether, at temperatures between 20° C. and 120° C., and forming derivatives of the resulting keto derivatives of the formula (XIII)

$$\underset{\underset{CH_3}{|}}{R^1-CO-\overset{\overset{CH_3}{|}}{C}-CHO} \quad (XIII)$$

in which $R^1$ has the abovementioned meaning, on the aldehyde group in the customary manner, such as, for example, by means of ethylene glycol in the presence of an inert organic solvent, such as, for example, toluene, and in the presence of a strong acid as a catalyst, such as, for example, p-toluenesulphonic acid, at temperatures between 80° C. and 110° C.

In some cases, it proves to be advantageous to introduce the radical $R^1$ or parts thereof only after the derivative has been formed on the aldehyde group (compare also the preparation examples).

The hydroxyethyl-azole derivatives of the formula (Ia) to be used as starting substances in carrying out process (b) according to the invention are compounds according to the invention.

Formula (III) provides a general definition of the hydroxylamine derivatives also to be used as starting substances for carrying out process (b) according to the invention. In this formula, $R^2$ preferably has the meanings which have already been mentioned as preferred for this substituent in connection with the description of the substances of the formula (I) according to the invention.

The hydroxylamine derivatives of the formula (III) are generally known compounds of organic chemistry.

The hydroxyethyl-azole derivatives of the formula (Ib) to be used as starting substances in carrying out process (c) according to the invention are compounds according to the invention.

Formula (IV) provides a general definition of the halides also to be used as starting substances for carrying out process (c) according to the invention. In this formula, $R^3$ preferably has those meanings which have already been mentioned as preferred for $R^2$, with the exception of hydrogen, in connection with the description of the substances of the formula (I) according to the invention.

The halides of the formula (IV) are generally known compounds of organic chemistry.

Formula (V) provides a general definition of the oxiranes to be used as starting substances in carrying out process (d) according to the invention. In this formula, $R^1$ preferably has those meanings which have already been mentioned as preferred for this substituent in connection with the description of the substances of the formula (I) according to the invention, and $R^3$ preferably has those meanings which have already been mentioned as preferred for $R^2$, with the exception of hydrogen, in connection with the description of the substances of the formula (I) according to the invention.

The oxiranes of the formula (V) are not yet known; however, they can be obtained in a generally known manner by epoxidizing keto-oxime derivatives of the formula (XIV)

$$\underset{\underset{CH_3}{|}}{R^1-CO-\overset{\overset{CH_3}{|}}{C}-CH=N-OR^3} \quad (XIV)$$

in which $R^1$ and $R^2$ have the abovementioned meaning, by processes (α) or (β) described above.

The keto-oxime derivatives of the formula (XIV) are the subject of Application Ser. Nos. 547,807, 503,102 and 503,220, supra; or they can be obtained in a known manner, for example by reacting 1-(N-morpholino)isobutene of the formula (XI) with chlorides of the formula (XII) in the presence of a solvent, such as, for example, diethyl ether, at temperatures between 20° C. and 120° C., and forming derivatives of the resulting keto derivatives of the formula (XIII) on the aldehyde group in the customary manner by means of hydroxylamine derivatives of the formula (III), such as, for example, methoxyhydroxylamine hydrochloride, in the presence of an inert organic solvent, such as, for example, ethanol, and in the presence of sodium acetate at temperatures between 80° C. and 110° C. In some cases, it proves advantageous to introduce the radial $R^1$ or parts thereof only after the derivative has been formed on the aldehyde group.

Formula (VI) provides a general definition of the azoles also to be used as starting substances for carrying out process (d) according to the invention. In this formula, X preferably represents the meanings which have already been mentioned as preferred for this substituent in connection with the description of the substances of the formula (I) according to the invention. M preferably represents hydrogen, sodium or potassium.

The azoles of the formula (VI) are generally known compounds of organic chemistry.

Process (a) according to the invention is carried out in the presence of a mixture of water and a water-miscible, inert organic solvent. Preferred possible organic solvents are alcohols.

Possible acids for process (a) according to the invention are all the inorganic and organic acids which can customarily be used. These include, preferably, hydrochloric acid, sulphuric acid, p-toluenesulphonic acid and acetic acid.

The reaction temperatures can be varied within a substantial range in carrying out process (a) according to the invention. In general, the reaction is carried out at temperatures between 30° C. and 120° C., preferably at the boiling point of the solvent used.

In carrying out process (a) according to the invention, 1 to 3 mols, preferably 2 mols, of acid are preferably employed per mol of the compound of the formula (II). The end products are isolated in the generally customary manner.

Preferred possible diluents for process (b) according to the invention are alcohols and water or mixtures of the two.

The reaction temperatures can be varied within a substantial range in process (b) according to the invention. In general, the reaction is carried out between 20° C. and 120° C., preferably between 50° C. and 100° C.

In carrying out process (b) according to the invention, 1 to 1.5 mols of hydroxylamine derivative of the formula (III) are preferably employed per mol of the compound of the formula (Ia). The compounds of the formula (I) are isolated by customary methods.

According to a preferred embodiment of process (b), the hydroxylamine derivatives of the formula (III) are used in the form of their salts, in particular as hydrochlorides, if appropriate in the presence of an acid-binding agent, such as, for example, sodium acetate (compare also the preparation examples).

Possible diluents for the reaction, according to the invention, in process (c) are inert organic solvents. These include, preferably, ethers, such as tetrahydrofuran and dioxane; aromatic hydrocarbons, such as toluene and benzene; in individual cases also chlorinated hydrocarbons, such as chloroform, methylene chloride or carbon tetrachloride; and hexamethylphosphoric acid triamide, acid amides, such as dimethylformamide, and sulphoxides, such as dimethylsulphoxide.

If appropriate, the reaction, according to the invention, in process (c) is carried out in the presence of a strong base. Strong bases include, preferably, alkali metal amides, hydrides, hydroxides and carbonates, such as, for example, sodium amide, carbonate, hydrocide or hydride and potassium amide, carbonate, hydroxide or hydride, and quaternary ammonium hydroxides and phosphonium hydroxides, such as, for example, tetramethylammonium hydroxide, benzyltrimethylammonium hydroxide of dibenzyl-dimethyl-ammonium hydroxide, and tetraphenylphosphonium hydroxide or methyltriphenyl-phosphonium hydroxide.

The reaction temperatures can be varied within a substantial range in process (c). In general, the reaction is carried out between 20° C. and 150° C., preferably at room temperature. In individual cases, it is advantageous to carry out the reaction at the boiling point of the solvent, for example between 60° C. and 100° C.

In carrying out process (c) according to the invention, 1 to 3 mols of halide of the formula (IV) are preferably employed per mol of the compound of the formula (Ib). To isolate the end products, the reaction mixture is freed from the solvent, and water and an organic solvent are added to the residue. The organic phase is separated off and worked up in the customary manner and the product is purified.

In a preferred embodiment of process (c), the reaction according to the invention is carried out in a two-phase system, such as, for example, aqueous sodium hydroxide solution or potassium hydroxide solution/toluene or methylene chloride, with addition of 0.01 to 1 mol of a phase transfer catalyst, such as, for example, an ammonium or phosphonium compound, the alcoholates being formed in the organic phase or at the interfaces and reacting with the halides in the organic phase.

Possible diluents for process (d) according to the invention are organic solvents which are inert under the reaction conditions. These include, preferably: alcohols, such as, for example, ethanol, methoxyethanol or propanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible bases for process (d) according to the invention are all the inorganic and organic bases which can customarily be used. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out process (d) according to the invention. In general, the reaction is carried out at temperatures between 0° C. and 200° C., preferably between 60° C. and 150° C.

In carrying out process (d) according to the invention, 1 to 2 mols of azole and, if appropriate, 1 to 2 mols of base are preferably employed per mole of oxirane of the formula (V). The end products are isolated in the generally customary manner.

Those acids which have already been mentioned as preferred acids in connection with the description of the acid addition salts according to the invention can preferably be used for the preparation of acid addition salts of the compounds of the general formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above can preferably be used for the preparation of metal salt complexes of the compounds of the general formula (I).

The metal salt complexes of the compounds of the general formula (I) can be obtained in a simple manner by customary processes, thus, for example, by dissolving the metal salt in alcohol, for example ethanol, and adding the solution to the compounds of the general formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating *Cochliobolus sativus* on barley and *Venturia inaequalis* on apples, and also for combating powdery mildew, *Septoria nodorum* and *Pyrenophora teres* on cereals and *Pyricularia oryzae* and *Pellicularia sasakii* on rice.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as. ULV cold mist and warm mist formulations.

These formulations are produced in known manner, for example by mixing the active compounds with extenders, that is, liquid solvents, liquified gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyarine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

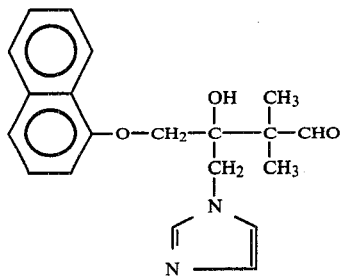

(Process a)

15 ml of concentrated hydrochloric acid are added to 22.7 g (0.059 mol) of 3-(1,3-dioxolan-2-yl)-2-(imidazol-1-yl-methyl)-3-methyl-1-(naphth-1-yl-oxy)-2-butanol in 150 ml of ethanol and 150 ml of water and the mixture is heated under reflux for 4 hours. The reaction mixture is then poured into saturated, aqueous sodium bicarbonate solution and extracted three times with methylene chloride. The combined organic phases are washed with water, dried over sodium sulphate and concentrated. The residue is taken up in ether/acetone and the product is filtered off with suction.

17.0 g (85.3% of theory) of 2,2-dimethyl-3-hydroxy-3-(imidazol-1-yl-methyl)-4-(naphth-1-oxy)-butanal of melting point 147° C. are obtained.

Preparation of the starting substance

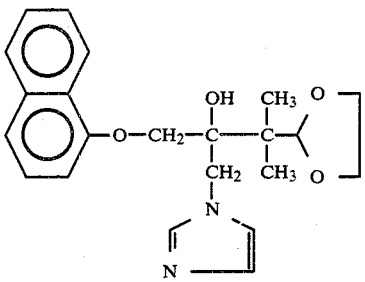

A solution of 53.5 g (0.17 mol) of 2-[2-(1,3-dioxolan-2-yl-prop-2-yl]-2-(naphth-1-yl-oxymethyl)-oxirane, 12.8 g (0.188 mol) of imidazole and 1.3 g of potassium hydroxide in 350 ml of absolute butanol is heated under reflux for 16 hours. The mixture is allowed to cool to room temperature and 500 ml of methylene chloride are added. The reaction mixture is washed twice with water. The organic phase is separated off, dried over sodium sulphate and concentrated. 350 ml of diisopropyl ether and ethyl acetate are added to the residue. The precipitate which has separated out is filtered off with suction.

38.3 g (59.4% of theory) of 3-(1,3-dioxolan-2-yl)-2-(imidazol-1-yl-methyl)-3-methyl-1-(naphth-1-yl-oxy)-2-butanol of melting point 126° C. are obtained.

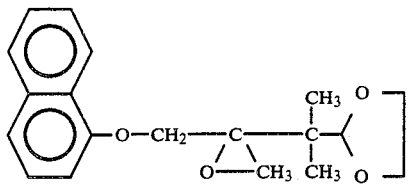

67.2 g (0.6 mol) of potassium tert.-butylate are added in portions to 131.1 g (0.596 mol) of trimethylsulphoxonium iodide in 120 ml of absolute dimethylformamide. The mixture is subsequently stirred at room temperature for 6 hours and a solution of 122 g (0.407 mol) of 2-(1,3-dioxolan-2-yl)-prop-2-yl naphth-1-yl-oxymethyl ketone in 550 ml of absolute tetrahydrofuran is then added. The reaction mixture is subsequently stirred overnight at room temperature and concentrated, the residue is taken up in methylene chloride and the mixture is washed twice with water, dried over sodium sulphate and concentrated. The residue is extracted by stirring in petroleum ether and the product is filtered off with suction.

107 g (83.7% of theory) of melting point 61° C. are obtained.

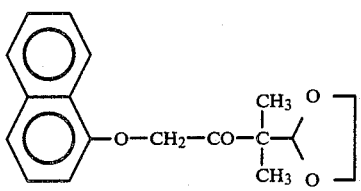

A solution of 141.5 g (0.735 mol) of 1-chloro-3-(1,3-dioxolan-2-yl)-3-methyl-2-butanone, 105.9 g (0.835 mol) of 1-naphthol and 122 g (0.882 mol) of potassium carbonate is 1000 ml of absolute ethyl methyl ketone is heated under reflux for 16 hours. The mixture is allowed to cool to room temperature and is filtered. The filtrate is concentrated, methylene chloride is added to the residue and the mixture is washed once with dilute sodium hydroxide solution and twice with water, dried over sodium sulphate and concentrated. The residue is extracted by stirring in petroleum ether and the product is filtered off with suction and dried.

122.6 g (55.6% of theory) of 2-(1,3-dioxolan-2-yl)-prop-2-yl naphth-1-yl-oxymethyl ketone of melting point 69° C. are obtained.

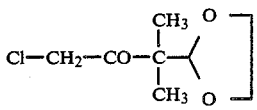

204 g (1.38 mol) of 4-chloro-2,2-dimethyl-3-ketobutanal are heated with 93 g (1.5 mol) of ethylene glycol and 0.7 g of p-toluenesulphonic acid in 400 ml of methylene chloride for 3 hours, using a water separator. The organic phase is extracted with 150 ml of 5% strength sodium hydroxide solution and then with 400 ml of water. The solvent is distilled off and the residue is distilled under a waterpump vacuum.

211 g (79.8% of theory) of 1-chloro-3-(1,3-dioxolan-2-yl)-3-methyl-butan-2-one of boiling point 127° C. to 128° C./14 mbar are obtained.

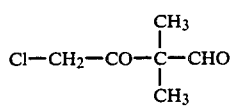

210 g (1.5 mols) of 1-(N-morpholino)-isobutene are added dropwise, at 5° C. in the course of one hour, to 169 g (1.5 mols) of chloroacetyl chloride dissolved in 350 ml of diethyl ether. When the addition has ended, the mixture is stirred for a further 3 hours, while cooling under reflux. The solution is poured onto 100 g of ice, the mixture is brought to pH 5 with aqueous sodium bicarbonate solution and the ether phase is separated off. The aqueous phase is extracted with 100 ml of diethyl ether, the organic phases are combined and dried over sodium sulphate, the solvent is distilled off and the residue is distilled under a waterpump vacuum.

136.4 g (61% of theory) of 4-chloro-2,2-dimethyl-3-keto-butanal of boiling point 95° C. to 98° C./14 mbar are obtained.

Example 2

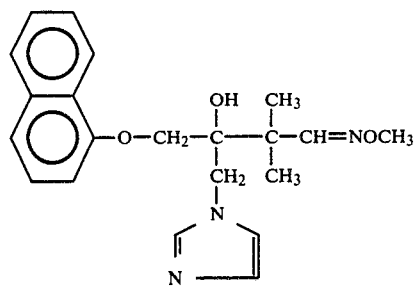

(Process b)

9 g (0.027 mol) of 2,2-dimethyl-3-hydroxy-3-(imidazol-1-yl-methyl)-4-(naphth-1-oxy)-butanal (Example 1) and 2.2 g (0.027 mol) of O-methyl-hydroxylamine hydrochloride are heated under reflux in 60 ml of ethanol for 16 hours. The reaction mixture is then concentrated, the residue is suspended in petroleum ether and the product is filtered off with suction and dried.

9 g (90.7% of theory) of 2-(imidazol-1-yl-methyl)-3-methoximinomethyl-3-methyl-1-(naphth-1-oxy)-2-butanol of melting point 177° C. to 178° C. are obtained.

The following compounds of the general formula (I) are obtained in an analogous manner corresponding to the process description according to the invention:

| Example No. | R$^1$ | X | Z | Melting point (°C.) or spectroscopic data |
|---|---|---|---|---|
| 3 | Cl—⟨phenyl⟩—OCH$_2$— | N | O | 107 |
| 4 | Cl—⟨phenyl⟩—OCH$_2$— | N | NOCH$_3$ | 144 |
| 5 | ⟨biphenyl⟩—OCH$_2$— | N | O | Oil/IR$_{CHCl_3}$: CHO = 1720 cm$^{-1}$ |
| 6 | ⟨naphthyl⟩—OCH$_2$ | N | O | Oil/IR$_{CHCl_3}$: CHO = 1722 cm$^{-1}$ |
| 7 | Cl—⟨phenyl⟩—CH$_2$—CH$_2$— | N | O | 105 |

-continued

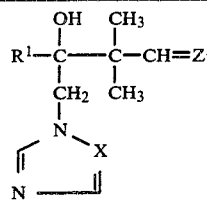

(I)

| Example No. | R¹ | X | Z | Melting point (°C.) or spectroscopic data |
|---|---|---|---|---|
| 8 | 2,4-dichlorophenyl-CH₂CH₂— | N | O | 136 |
| 9 | 4-chlorophenyl-C≡C— | N | O | 119 |
| 10 | 4-chlorophenyl-C≡C— | N | NOCH₃ | 121 |
| 11 | 4-biphenylyl-C≡C— | N | O | 147 |
| 12 | 4-biphenylyl-C≡C— | N | NOCH₃ | 151 |
| 13 | 2,4-dichlorophenyl-C≡C— | N | NOCH₃ | 93 |
| 14 | 3,4-dichlorophenyl— | N | O | 147–151 |
| 15 | 3,4-dichlorophenyl— | N | NOCH₃ | 96–101 |
| 16 | 4-chlorophenyl-CH₂CH₂— | CH | O | 127 |
| 17 | 3-chloro-4-trifluoromethylphenyl-SCH₂— | N | NOCH₃ | Oil/¹H—NMR$_{CDCl_3}$: = 4.45 ppm for —CH₂—N(triazole) |

-continued $$\begin{array}{c} \text{OH} \quad \text{CH}_3 \\ R^1-\overset{|}{\underset{|}{C}}-\overset{|}{\underset{|}{C}}-CH=Z \\ CH_2 \quad CH_3 \\ | \\ N \\ \diagup \diagdown \\ N \quad X \\ \diagdown \diagup \end{array}$$ (I)

| Example No. | R¹ | X | Z | Melting point (°C.) or spectroscopic data |
|---|---|---|---|---|
| 18 | 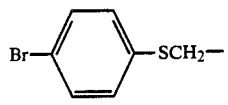 4-Br-C₆H₄-S-CH₂- | N | NOCH₃ | Oil/¹H—NMR$_{CDCl_3}$: = 4.42 ppm for -CH₂-N(triazole) |
| 19 | 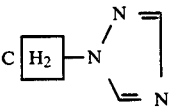 4-Br-C₆H₄-S-CH₂- | N | O | Oil/IR$_{CHCl_3}$: CHO = 1720 cm⁻¹ |
| 20 | 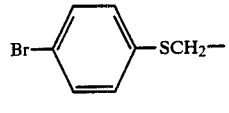 4-Cl-C₆H₄-S-CH₂- | CH | NOCH₃ | Oil/¹H—NMR$_{CDCl_3}$: = 4.13 ppm for -CH₂-N(imidazole) |
| 21 | 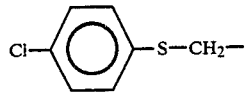 4-Br-C₆H₄-S-CH₂- | CH | NOCH₃ | Oil/¹H—NMR$_{CDCl_3}$: = 4.15 ppm for -CH₂-N(imidazole) |
| 22 | 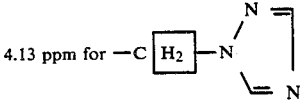 4-Cl-C₆H₄-CH₂-CH₂- | N | NOCH₃ | Oil/¹H—NMR$_{CDCl_3}$: = 4.35 ppm for -CH₂-N(triazole) |
| 23 | 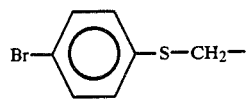 4-Cl-C₆H₄-CH₂-CH₂- | N | NOC₄H₉ | Oil/¹H—NMR$_{CDCl_3}$: = 4.35 ppm for -CH₂-N(triazole) |
| 24 | 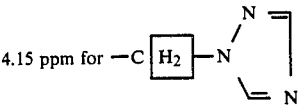 2,4-Cl₂-C₆H₃-O-CH₂- | N | NOCH₃ | 119 |
| 25 | 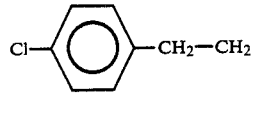 3,4-Cl₂-C₆H₃- | N | NOC₂H₅ | 127-29 |
| 26 | 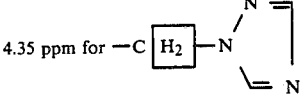 3,4-Cl₂-C₆H₃- | N | NOC₄H₉—n | 138-40 |

-continued

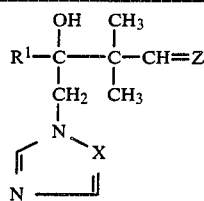

(I)

| Example No. | R¹ | X | Z | Melting point (°C.) or spectroscopic data |
|---|---|---|---|---|
| 27 | 3,4-dichlorophenyl | N | NOCH₂—CH=CH₂ | 140–42 |
| 28 | 4-Cl-C₆H₄-CH₂CH₂— | N | NOCH₂-(4-Cl-C₆H₄) | 125–27 |
| 29 | 4-Cl-C₆H₄-CH₂CH₂— | N | 2,4-diCl-C₆H₃-CH₂ON (NOCH₂-2,4-diCl-phenyl) | 97 |
| 30 | 3,4-diCl-C₆H₃-OCH₂— | N | NOCH₂-(4-Cl-C₆H₄) | 89–90 |
| 31 | 3,4-diCl-C₆H₃-OCH₂— | N | NOCH₂-(2,4-diCl-C₆H₃) | 72 |
| 32 | 4-Cl-C₆H₄-SCH₂— | N | NOCH₃ | viscous oil |
| 33 | 4-Cl-C₆H₄-SCH₂— | N | NOCH₂—CH=CH₂ | 100–01 |
| 34 | CH₃ | N | NOCH₂-(2,4-diCl-C₆H₃) | viscous oil |
| 35 | biphenyl-4-yl | N | NOCH₃ | 55–57 |
| 36 | biphenyl-4-yl | N | NOCH₂—CH=CH₂ | 75 |

-continued $$R^1-\underset{\underset{CH_2}{|}}{\overset{\overset{OH}{|}}{C}}-\underset{\underset{CH_3}{|}}{\overset{\overset{CH_3}{|}}{C}}-CH=Z \quad (I)$$

$$\underset{N\diagup\diagdown}{N}X$$

| Example No. | R¹ | X | Z | Melting point (°C.) or spectroscopic data |
|---|---|---|---|---|
| 37 | 4-Cl-C₆H₄- | N | NOCH₃ | 96–101 |
| 38 | 4-Cl-C₆H₄- | N | NOC₃H₇—n | 112–14 |
| 39 | 4-Cl-C₆H₄- | N | NOCH₂-cyclohexyl | 130–33 |
| 40 | 4-Cl-C₆H₄- | N | NOC₄H₉—n | 124–30 |
| 41 | C₃H₇n- | N | NOCH₂-(4-Cl-C₆H₄) | viscous oil |
| 42 | C₃H₇n- | N | NOCH₂-(2,4-Cl₂-C₆H₃) | viscous oil |
| 43 | C₂H₅— | N | NOCH₂-(4-Cl-C₆H₄) | $n_D^{20} = 1.5456$ |
| 44 | C₂H₅— | N | NOCH₂-(2,4-Cl₂-C₆H₃) | viscous oil |
| 45 | C₄H₉n- | N | NOCH₂-cyclohexyl | $n_D^{20} = 1.5021$ |
| 46 | C₄H₉n- | N | NOCH₂-(4-Cl-C₆H₄) | $n_D^{20} = 1.5353$ |
| 47 | C₄H₉n- | N | NOCH₂-(2,4-Cl₂-C₆H₃) | $n_D^{20} = 1.5438$ |

Use Examples

The substances shown below are used as comparison compounds in the use examples which follow:

(A) 2,4-dichloro-phenyl compound: Cl, Cl substituted phenyl—O—CH₂—C(OH)(CH₂-triazolyl)—C(CH₃)₃

(B) 4-chloro-phenyl compound: Cl substituted phenyl—O—CH₂—C(OH)(CH₂-triazolyl)—C(CH₃)₃

Example A

*Cochliobolus sativus* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 7, 8, 3 and 4.

Example B

Venturia test (apple)/protective/

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 16 and 5.

It is understood that the specification and examples are illustrative but not limitative of the present invention and that other embodiments within the spirit and scope of the invention will suggest themselves to those skilled in the art.

We claim:

1. A hydroxyethyl-azole derivative of the formula $$R^1-\underset{\underset{\underset{N\diagdown_X}{|}}{\overset{|}{CH_2}}}{\overset{\overset{OH}{|}}{C}}-\underset{\overset{|}{CH_3}}{\overset{\overset{CH_3}{|}}{C}}-CH=NOR^2$$

(with triazole/imidazole ring attached via $CH_2$)

in which $R^1$ represents alkyl with 1 to 6 carbon atoms or the grouping Ar—Y—,

Ar represents naphthyl, or represents phenyl which is unsubstituted, monosubstituted or polysubstituted by identical or different substituents selected from the group consisting of halogen; alkyl with 1 to 4 carbon atoms; alkoxy with 1 to 2 carbon atoms; alkylthio with 1 to 2 carbon atoms; nitro; halogenoalkyl; halogenoalkoxy, said halogenoalkyl and halogenoalkoxy having 1 to 2 carbon atoms and 1 to 5 identical or different halogen atoms; the —CH=NOR² radical; unsubstituted phenyl; unsubstituted phenoxy; unsubstituted benzyl; unsubstituted benzyloxy; substituted phenyl; substituted phenoxy; substituted benzyl; and substituted benzyloxy, said substituted phenyl, substituted phenoxy, substituted benzyl and substituted phenoxy being substituted by a substituent selected from the group consisting of halogen and $C_1$-$C_2$ alkyl, X represents a nitrogen atom or the CH group, Y represents a direct bond or the grouping —CH₂—, —CH₂CH₂—, —OCH₂—, —SCH₂—, —CH=CH— or —C≡C—, and $R^2$ represents hydrogen, or represents $C_1$-$C_6$ straight-chain alkyl; $C_1$-$C_6$ branched chain alkyl; or represents $C_2$ to $C_6$ alkenyl; $C_2$ to $C_6$ alkinyl; or represents phenylalkyl which has 1 or 2 carbon atoms in the alkyl part and is unsubstituted or monosubstituted or polysubstituted by identical or different substituents on the phenyl, said substituents selected from the group consisting of halogen; alkyl with 1 to 4 carbon atoms; alkoxy with 1 to 2 carbon atoms; alkylthio with 1 to 2 carbon atoms; nitro; halogenoalkyl and halogenoalkoxy, said halogenoalkyl and halogenalkoxy having 1 to 2 carbon atoms and 1 to 5 identical or different halogen atoms; the —CH=NOR² radical, unsubstituted phenyl; unsubstituted phenoxy; unsubstituted benzyl; unsubstituted benzyloxy; substituted phenyl; substituted phenoxy, substituted benzyl and substituted benzyloxy, said substituted phenyl, substituted phenoxy, substituted benzyl and substituted benzyloxy being substituted by a substituent selected from the group consisting of halogen and $C_1$-$C_2$ alkyl or $R^2$ represents cycloalkylmethyl which has 5 to 6 carbon atoms in the cycloalkyl part and is unsubstituted or mono-, di- or tri-substituted by identical or different alkyl radicals with 1 to 3 carbon atoms, or an addition product thereof with an acid or metal salt.

2. A compound or addition product according to claim 1, in which

Ar represents naphthyl, or represents phenyl which is unsubstituted or mono-, di- or tri-substituted by identical or different substituents selected from the group consisting of fluorine, chlorine, methyl, trifluoromethyl, trifluoromethoxy, trifluoromethylthio, methoximinomethyl, ethoximinomethyl, allyloximinomethyl, phenyl, phenoxy, benzyl and benzyloxy, said phenyl, phenoxy, benzyl and benzyloxy being unsubstituted or substituted by chlorine and/or methyl; and $R^2$ represents hydrogen, methyl, ethyl, n-propyl, n-butyl, allyl or propargyl, or represents benzyl which is unsubstituted or mono-, di- or tri-substituted by identical or different substituents selected from the group consisting of fluorine, chlorine, methyl, trifluoromethyl and trifluoromethoxy, or $R^2$ represents cyclohexylmethyl which is unsubstituted or substituted by methyl or ethyl.

3. A compound according to claim 1, wherein such compound is 1-(2,4-dichlorophenyl)-4-methoximinomethyl-4-methyl-3-(1,2,4-triazol-1-yl-methyl)-pent-1-yn-3-ol of the formula

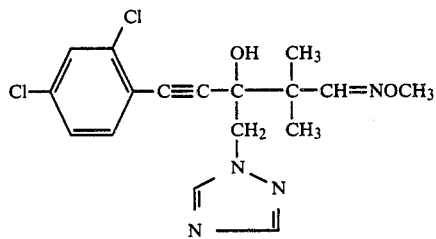

or an addition product thereof with an acid or metal salt.

4. A compound according to claim 1, wherein such compound is 1-(3,4-dichlorophenyl)-4-methoximinomethyl-4-methyl-3-(1,2,4-triazol-1-yl-methyl)-pent-1-yn-3-ol of the formula

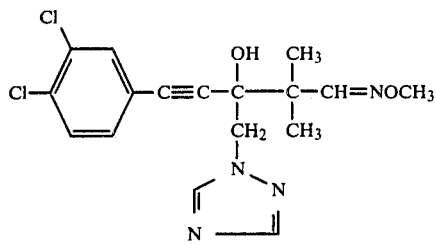

or an addition product thereof with an acid or metal salt.

5. A compound according to claim 1, wherein such compound is 1-(4-bromophenylthio)-3-methoximinomethyl-3-methyl-2-(1,2,4-triazol-1-yl-methyl)butan-2-ol of the formula

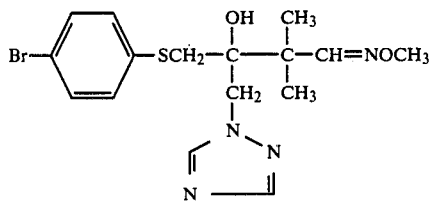

or an addition product thereof with an acid or metal salt.

6. A compound according to claim 1, wherein such compound is 1-(4-chlorophenyl)-4-methoximinomethyl-4-methyl-3-(1,2,4-triazol-1-yl-methyl)-pent-1-yn-3-ol

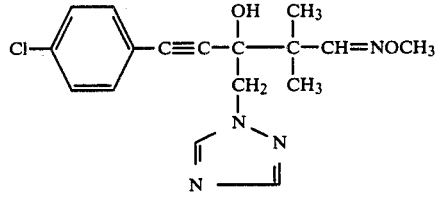

or an addition product thereof with an acid or metal salt.

7. A fungicidal composition comprising a fungicidally effective amount of a compound or addition product according to claim 1 in admixture with a diluent.

8. A method of combating fungi which comprises administering to such fungi or a fungus habitat a fungicidally effective amount of a compound or addition product according to claim 1.

9. The method according to claim 8, wherein such compound is 1-(2,4-dichlorophenyl)-4-methoximinomethyl-4-methyl-3-(1,2,4-triazol-1-yl-methyl)-pent-1-yn-3-ol,
1-(3,4-dichlorophenyl)-4-methoximinomethyl-4-methyl-3-(1,2,4-triazol-1-yl-methyl)-pent-1-yn-3-ol
1-(4-bromophenylthio)-3-methoximinomethyl-3-methyl-2-(1,2,4-triazol-1-yl-methyl)-butan-2-ol or
1-(4-chlorophenyl)-4-methoximinomethyl-4-methyl-3-(1,2,4-triazol-1-yl-methyl)-pent-1-yn-3-ol or an addition product thereof with an acid or metal salt.

* * * * *